United States Patent [19]

Lee et al.

[11] Patent Number: 4,948,472

[45] Date of Patent: Aug. 14, 1990

[54] EXTRACTIVE DISTILLATION OF HYDROCARBON MIXTURES EMPLOYING MIXED SOLVENT

[75] Inventors: Fu Ming Lee; Ronald E. Brown, both of Bartlesville, Okla.

[73] Assignee: Phillips Petroleum Company, Bartlesville, Okla.

[21] Appl. No.: 378,734

[22] Filed: Jul. 12, 1989

[51] Int. Cl.$^5$ .............................................. B01D 3/40
[52] U.S. Cl. ..................................... 203/55; 203/56; 203/58; 203/64; 203/70; 585/865; 585/867
[58] Field of Search .................... 203/51, 52, 58, 56, 203/55, 63, 64, 68, 70; 208/313; 585/800, 865, 867, 833

[56] References Cited

U.S. PATENT DOCUMENTS

| | | | |
|---|---|---|---|
| 2,508,723 | 5/1950 | Mayland et al. | 585/866 |
| 2,679,472 | 5/1954 | Tooke | 203/60 |
| 2,695,322 | 11/1954 | Weedman | 585/839 |
| 2,736,755 | 2/1956 | Reuter et al. | 55/84 |
| 2,771,494 | 11/1956 | Weedman | 585/836 |
| 2,786,804 | 3/1957 | Nelson | 203/60 |
| 2,809,925 | 10/1957 | Nelson | 203/60 |
| 2,839,452 | 6/1958 | Nelson | 203/60 |
| 2,846,485 | 8/1958 | Meason et al. | 585/866 |
| 2,891,894 | 6/1959 | Cier et al. | 203/60 |
| 3,034,969 | 5/1962 | Makin, Jr. | 203/60 |
| 3,301,911 | 1/1967 | Boatright | 585/866 |
| 3,349,009 | 10/1967 | Ruehlen | 203/67 |
| 3,366,568 | 1/1968 | Eisenlohr et al. | 208/313 |
| 3,415,742 | 12/1968 | Eisenlohr et al. | 208/323 |
| 3,591,490 | 7/1971 | Müller et al. | 208/313 |
| 3,898,297 | 8/1975 | Sampson et al. | 585/866 |
| 4,053,369 | 10/1977 | Cines | 203/52 |
| 4,081,332 | 3/1978 | Hein | 203/56 |
| 4,278,505 | 6/1981 | Danulat et al. | 203/59 |
| 4,349,416 | 9/1982 | Brandt et al. | 203/64 |
| 4,396,492 | 8/1983 | Bardasz | 203/7 |
| 4,498,980 | 2/1985 | Forte | 208/321 |
| 4,514,262 | 4/1985 | Berg | 203/64 |
| 4,676,874 | 6/1987 | Berg et al. | 203/56 |

OTHER PUBLICATIONS

Robert C. Weast et al., "CRC Handbook of Chemistry," 67th ed., 1986–1987, pp. E-49-E-51.
"Extractive Distillation Saves Energy", by Ian Sucksmith, Chemical Engineering, Jun. 29, 1982, pp. 91–95.
"Handbook of Separation Techniques for Chem. Engineers", by Philip Schweitzer, McGraw-Hill Book Co., 1979, pp. 1–135 to 1–143.
"Perry's Chemical Engineers' Handbook", 6th Edition, McGraw Hill Book Co., 1984, pp. 13-53 to 13-57.

Primary Examiner—Virginia Manoharan
Attorney, Agent, or Firm—K. K. Brandes

[57] ABSTRACT

A mixture of (a) at least one N-alkyl-2-pyrrolidone (preferably N-methyl-2-pyrrolidone) and (b) at least one glycol compound (preferably ethylene glycol or tetraethylene glycol) is used as solvent in the extractive distillation of a feed mixture of cycloalkane(s) (in particular cyclohexane) and close-boiling alkane(s).

20 Claims, 1 Drawing Sheet

EXTRACTIVE DISTILLATION OF HYDROCARBON MIXTURES EMPLOYING MIXED SOLVENT

BACKGROUND OF THE INVENTION

In one aspect, this invention relates to the separation of saturated cycloaliphatic hydrocarbons (cycloalkanes, naphthenes) from close-boiling paraffinic hydrocarbons (alkanes, paraffins) by extractive distillation. In another aspect, this invention relates to the use of mixtures of pyrrolidone compounds and glycol compounds as solvent (also referred to as extractant or entrainer) in the aforementioned extractive distillation.

Extractive distillation is a well known technique for separating mixtures of components having a relative volatility close to unity (i.e., having nearly equal volatility and having nearly the same boiling point). It is quite difficult to separate the components in such mixtures by conventional fractional distillation.

In extractive distillation, a solvent is introduced into a distillation column above the entry point of the feed mixture which is to be separated. The solvent affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, June 28, 1982, pages 91–95, the disclosure of which is herein incorporated by reference. Other literature sources on extractive distillation techniques include the "Handbook of Separation Techniques for Chemical Engineers" by Philip A. Schweitzer, McGraw-Hill Book Company, 1979, pages 1-135 to 1-143; and Perry's Chemical Engineers Handbook, 6th Edition, McGraw-Hill Book Company, 1984, pages 13-53 to 13-57, the disclosures of which are herein incorporated by reference.

The separation of naphthenes (cycloparaffins or cycloalkanes), in particular cyclohexane, from close-boiling paraffins (alkanes) by extractive distillation is known and has been described in the patent literature, such as in U.S. Pat. Nos. 2,508,723; 2,771,494; 2,846,485; 2,891,894; 3,034,969 and 4,053,369, the disclosures of which are herein incorporated by reference. However, there is an ever present need to develop more selective solvents than those presently known in the extractive distillation of mixtures of close-boiling paraffins and naphthenes. In particular, it is highly desirable to develop improved extractive distillation processes for producing cyclohexane of high purity, which is a starting material for making nylon and other useful polymeric materials.

SUMMARY OF THE INVENTION

It is an object of this invention to provide a process for separating mixtures of close-boiling naphthenes (cycloalkanes) and paraffins (alkanes) by extractive distillation employing a mixed solvent. It is another object of this invention to produce cyclohexane of high purity from a mixture comprising cyclohexane and close-boiling isoparaffins (i.e., isoparaffins having nearly the same volatility as cyclohexane) by extractive distillation employing a mixed solvent. Other objects and advantages will be apparent from the detailed description of the invention and the appended claims.

In accordance with this invention, in a process for separating at least one cycloalkane (naphthene) containing 5–10 carbon atoms per molecule from at least one close-boiling alkane (paraffin), i.e., one or a plurality of alkanes having nearly the same boiling point at atmospheric pressure conditions as said cycloalkane, by extractive distillation of a feed comprising said at least one cycloalkane and said at least one alkane, the improvement comprises using as solvent (also referred to as extractant or entrainer) a mixture of (a) at least one N-alkyl-2-pyrrolidone, wherein the alkyl group can contain 1–3 carbon atoms per molecule and (b) at least one glycol compound having the general chemical formula of

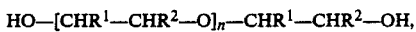

$HO-[CHR^1-CHR^2-O]_n-CHR^1-CHR^2-OH$, wherein n can be 0, 1, 2, 3, or 4, and $R^1$ and $R^2$ can be independently selected from the group consisting of hydrogen and the methyl group.

In a preferred embodiment, the feed cycloalkane is cyclohexane. In another preferred embodiment, component (a) of the solvent is N-methyl-2-pyrrolidone, and $R^1$ and $R^2$ in the formula of the glycol compound (b) are both H. In a particularly preferred embodiment, said glycol compound is ethylene glycol ($HO-CH_2-CH_2-OH$) or tetraethylene glycol ($HO-[CH_2-CH_2-O]_3-CH_2-CH_2-OH$). In a more preferred embodiment, the solvent consists essentially of (a) and (b).

DETAILED DESCRIPTION OF THE INVENTION

Figure 1:
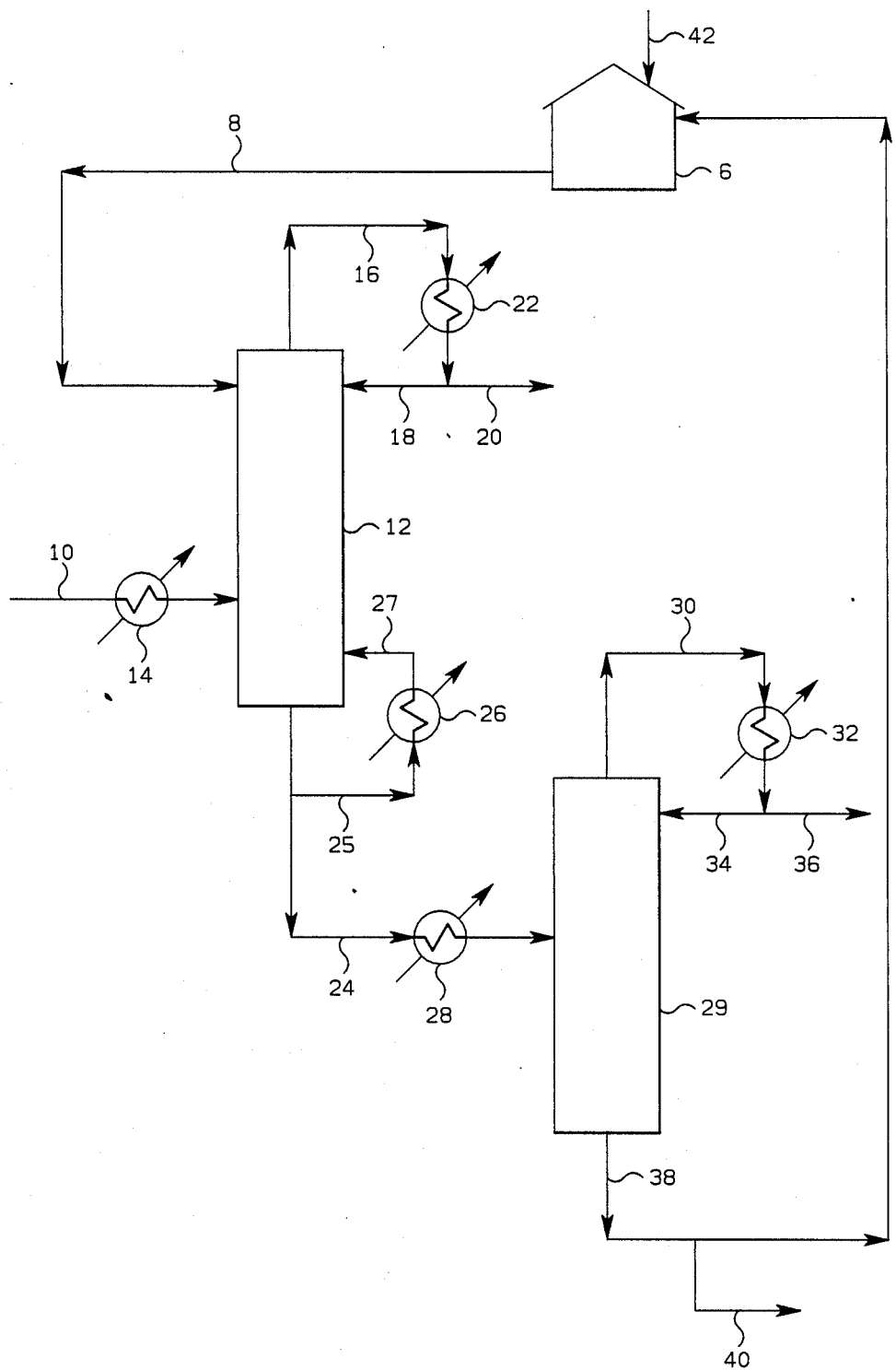
FIG. 1 illustrates the extractive distillation process of this invention.

In an extractive distillation process, an agent (called "solvent" or "extractant" or "entrainer") is added to a feed mixture of components to be separated so that the relative volatilities of the components of the mixture are changed such that a sufficient difference in volatility of the components results and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative volatilities of the components in a mixture, and will allow for the separation of components in a mixture with fewer distillation stages, lower amount of reflux and higher product purity.

Any hydrocarbon feed which contains at least one cycloalkane (naphthene) containing 5–9 carbon atoms per molecule and at least one close-boiling alkane (preferably containing 5–10 carbon atoms per molecule; more preferably branched alkane or isoparaffin) can be used in the process of this invention. Preferably, the boiling point (at atmospheric pressure conditions, i.e., at about 1 atm.) of the cycloalkane(s) and alkane(s) to be separated by extractive distillation is in the range of from about 80° to about 350° F., more preferably about 100°–300° F. Generally, the boiling points of the cycloalkane(s) and the alkane(s) differ by about 0.2–10° F. (preferably about 0.5°–5° F.), at about 1 atm.

Non-limiting examples of suitable cycloalkanes are cyclopentane, cyclohexane, methylcyclopentane, cycloheptane, 1,1-dimethylcyclopentane, 1,2-dimethylcyclopentane, 1,3-dimethylcyclopentane, ethylcyclopentane, methylcyclohexane, 1,1-dimethylcyclohexane, 1,2-dimethylcyclohexane, 1,3-dimethylcyclohexane, ethylcyclohexane, cyclooctane, and the like. Presently preferred are cyclohexane and methylcyclopentane.

Non-limiting examples of alkanes are n-pentane, n-hexane, 2-methylpentane, 3-methylpentane, n-heptane, 2,2-dimethylpentane, 2,3-dimethylpentane, 2,4-dimethylpentane, 3,3-dimethylpentane, 2-methylhexane, 3-methylhexane, 2,2,3-trimethylbutane, n-octane, 2-methyloctane, n-nonane, and the like. Presently preferred are 2,3-dimethylpentane and n-hexane.

Examples of component (a) of the solvent include N-methyl-2-pyrrolidone (presently preferred), N-ethyl-2-pyrrolidone N-propyl-2-pyrrolidone and mixtures thereof. Non-limiting examples of component (b) include ethylene glycol, diethylene glycol, triethylene glycol, tetraethylene glycol (presently most preferred) and pentaethylene glycol, and mixtures thereof.

Any suitable weight ratio of component (b) to component (a) in the solvent (also called extractant) can be employed in the extractive distillation process of this invention. Preferably, the weight ratio of component (b) to component (a) is in the range of from about 0.2:1 to about 30:1, more preferably from about 1:1 to about 10:1. The preferred component (a) is N-methyl-2-pyrrolidone, and the preferred component (b) is ethylene glycol or tetraethylene glycol, more preferably tetraethylene glycol. In a preferred embodiment, the solvent contains about 1–3 weight-% water.

Any suitable weight ratio of the solvent to any of the above-described hydrocarbon-containing feed mixtures can be employed. Preferably, the solvent to feed weight ratio is in the range of from about 0.5:1 to about 50:1, more preferably from about 3:1 to about 20:1.

Any suitable reflux ratio (i.e., the weight ratio of the portion of condensed vapor which is returned to the distillation column to the portion of condensed vapor which is withdrawn as distillate) can be employed in the processes of this invention. Generally, the reflux ratio is in the range of from about 0.1:1 to about 100:1, preferably in the range of from about 0.5:1 to about 50:1, more preferably in the range of from about 1:1 to about 20:1.

Any suitable feed entry location can be selected for the processes of this invention. Generally, the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected for the processes of this invention. Generally, the solvent entry location is in the range of from about 50 to about 99 percent of the total height of the packed or trayed column (i.e., within the upper half of the packed column), preferably in the range of from about 70 to about 99 percent, more preferably in the range of from about 80 to about 99 percent.

Any suitable temperature in the distillation vessel (containing primarily the higher boiling feed components and the solvent) can be employed in the processes of this invention. The temperature is generally in the range of from about 100° to about 400° F., preferably in the range of from about 150° to about 320° F. The extractive distillation column is generally heated (more near the bottom, and less near the top). Generally, the temperature at the top of the column where the vapor exits into the condenser is in the range of from about 100° to about 300° F., preferably in the range of from about 150° to about 250° F. Solvent and feed are generally preheated (generally to a temperature close to the column temperature of the corresponding entry point) before they are introduced into the packed or trayed column. Any suitable pressure can be employed during the extractive distillation. Generally, the pressure is about 5 to about 100 psig, preferably about 8 to about 20 psig.

The overhead product (withdrawn from the top of the column) generally contains a smaller volume percentage of cycloalkane(s) (preferably cyclohexane) than the feed and a larger volume percentage of alkane(s) (preferably isoalkanes) than the feed. Generally, the bottoms product (a portion of which can be reheated and recycled to the lower portion of the column) contains more of cycloalkane(s) than the feed, and less of the alkane(s) (preferably isoalkanes) than the feed. Furthermore, the bottoms product contains substantially all of the added solvent, which can be separated from the other bottoms product component by distillation or other suitable separating means and then be recycled to the extractive distillation column.

Any suitable total column height, packed column height, column diameter and number of trays in the extraction distillation column can be employed in the process of this invention. The exact dimensions and column designs depend on the scale of the operation, the exact feed composition, the exact solvent composition, the desired recovery and degree of purity of the various hydrocarbon products, and the like, and can be determined by those having ordinary skills in the art.

The invention can be better understood by reference to FIG. 1 and the following description of a preferred embodiment of the invention. The feed mixture comprising naphthenic and paraffinic hydrocarbons is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in paraffinic hydrocarbons (alkanes) is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottoms product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottom stream flow through conduit 24 such that the feed mixture introduced into distillation column 12 will be fractionated to yield an overhead stream which is enriched in paraffinic hydrocarbons and a bottoms stream predominantly comprising the naphthenic hydrocarbons and the solvent.

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising naphthenic hydrocarbons is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, i.e., naphthenic compounds (preferably cyclohexane) of high purity (preferably higher than 95%), through conduit 36.

A bottoms stream predominantly comprising the solvent is withdrawn from a lower portion of distillation column 29 through conduit 38. A portion of this bottoms stream is preferably routed back to solvent storage 6 and then recycled to distillation column 12, while another portion of the bottoms stream is heated in a reboiler (not shown) and returned to the lower portion of column 29. From time to time impurities which may build up in the solvent can be removed from the system by removing a small purge stream through conduit 40. Solvent lost through the purge stream or through other processing losses may be made up by a makeup stream passing through conduit 42 and into solvent storage 6.

The following examples are presented to further illustrate the invention and are not to be considered unduly limiting the scope of this invention.

EXAMPLE I

This example demonstrates the superiority as extractant of a mixture of a glycol compound and N-methyl-2-pyrrolidone (NMP) versus each component alone.

To a hydrocarbon mixture of 85 weight percent cyclohexane and 15 weight percent 2,3-dimethylpentane (2,3-DMP) was added an extractive solvent: either NMP or ethylene glycol (EG) or tetraethylene glycol (TTEG) or mixtures of the above, at a solvent:feed weight ratio of 7:1. The total mixture (including the extractive solvent) was heated under reflux conditions for about 20–30 minutes in a distillation flask equipped with a reflux condenser. Then a small sample was withdrawn by means of a septum from the flask containing the liquid phase of the equilibrium system, and a sample of the condensed vapor was withdrawn by means of a septum located just below the reflux condenser. Both samples were analyzed, and the mole fractions of 2,3-DMP and cyclohexane in the liquid phase and in the condensed vapor phase were determined. The relative volatility R was calculated as follows:

$$R = \frac{Y1/Y2}{X1/X2} = \frac{Y1/X1}{Y2/X2};$$

wherein Y1 and Y2 are the mole fractions of 2,3-DMP and cyclohexane, respectively, in the vapor phase; and X1 and X2 are the mole fractions of 2,3-DMP and cyclohexane, respectively, in the liquid phase. Test results are summarized in Table 1.

TABLE I

| Added Solvent | Relative Volatility R |
| --- | --- |
| NMP | 1.07 |
| EG | 1.02[1] |
| 25 wt-% EG + 75 wt-% NMP | 1.15 |
| 50 wt-% EG + 50 wt-% NMP | 1.22[1] |
| TTEG | 1.10 |
| 50 wt-% TTEG + 50 wt-% NMP | 1.19 |
| 75 wt-% TTEG + 25 wt-% NMP | 1.23[1] |

[1]Two liquid phases were present in these runs (the other runs contained 1 liquid phase).

Test data summarized in Table I indicate that mixtures of ethylene glycol+NMP and mixtures of tetraethylene glycol+NMP would be more effective as extractants in the separation of cyclohexane and close-boiling isoparaffin(s) by extractive distillation than either ethylene glycol or tetraethylene glycol or N-methyl-2-pyrrolidone alone. These test data also indicate that mixtures containing at least 50% weight-% of the glycol compound would be most effective as extractants.

EXAMPLE II

This example further illustrates the superiority of mixtures of NMP and glycol compounds as extractants when employed in the separation of an alkane from a cycloalkane. The composition of the hydrocarbon feed is given in Table II.

TABLE II

| Feed Component | Wt. % | Boil. Pt. (°F.) |
| --- | --- | --- |
| 2,2-Dimethylbutane | 0.1 | 136.4 |
| 3-Methyl-pentane | 5.3 | 146 |
| n-Hexane | 19.3 | 155.7 |
| Methylcyclopentane | 51.6 | 161.3 |
| Benzene | 15.5 | 176.2 |
| Cyclohexane | 8.2 | 177.3 |

A solvent (either was added to the above-described feed, and the entire mixture of feed and solvent was heated under reflux conditions in the apparatus described in Example I. Samples of the liquid phase and of the condensed vapor were taken and analyzed. Relative volatility α was calculated as follows:

$$\alpha = \frac{Y3/Y4}{X3/X4} = \frac{Y3/X3}{Y4/X4},$$

wherein the mole fractions of n-hexane in the vapor phase and liquid phase, respectively, are Y3 and X3, respectively; and the mole fractions of methylcyclopentane in the vapor phase and liquid phase, respectively, are Y4 and X4, respectively. Test results are summarized in Tables III.

TABLE III

| Solvent:Feed Weight Ratio | Added Solvent | Relative Volatility α |
| --- | --- | --- |
| 3:1 | NMP | 1.34 |
| 3:1 | TTEG | 1.14 |
| 3:1 | NMP + TTEG (1:1 weight ratio) | 1.34 |
| 4.1:1 | NMP | 1.36 |
| 4.1:1 | TTEG | 1.17 |
| 4.1:1 | NMP + TTEG (1:1 weight ratio) | 1.38 |
| 5:1 | NMP | 1.37 |
| 5:1 | TTEG | 1.19 |
| 5:1 | NMP + TTEG (1:1 weight ratio) | 1.44 |

Test results summarized in Table III indicate that mixtures of N-methyl-2-pyrrolidone and tetraethylene glycol would be more effective than the single component solvents as extractants in the separation of n-hexane from methylcyclopentane, at a solvent to feed weight ratio of about 4:1 or higher. Based on the trends in the above test data, it is concluded that a solvent to feed ratio of about 7:1 would be more effective than a ratio of about 4-5:1.

EXAMPLE III

This example illustrates the effect of the solvent to feed ratio and the effect of water on the relative volatility R (defined in Example I) for a feed mixture of 85 weight-% cyclohexane and 15 weight-% 2,3-dimethylpentane. The employed solvent in all tests was a mixture of 50 weight-% NMP and 50 weight-% ethylene glycol. Test results are summarized in Table IV.

TABLE IV

| Temp. (°F.) | Solvent: Feed Wt. Ratio | Wt-% H₂O in Liquid Phase | Relative Volatility R |
| --- | --- | --- | --- |
| 180 | 1:1 | 0 | 0.90 |
| 188 | 3:1 | 0 | 1.03 |
| 188 | 5:1 | 0 | 1.17 |
| 197 | 7:1 | 0 | 1.22 |
| 193 | 7:1 | 0.9 | 1.23 |
| 183 | 7:1 | 2.5 | 1.23 |
| 175 | 7:1 | 4.2 | 1.17 |

Test results in Table IV indicate that a high solvent to feed ratio is beneficial regarding the effectiveness of a mixed NMP/ethylene glycol solvent in the extractive distillation of the feed. Furthermore, the test data in Table IV indicate that the presence of relatively small amounts of water (about 1-3 weight-%) would be beneficial in an extractive distillation because the boiling temperature (and thus the operating temperature of the extractive distillation) would be lowered without significantly affecting the relative volatility.

Reasonable variations, modifications and adaptations for various usages and conditions can be made within the scope of the disclosure and the appended claims, without departing from the scope of this invention.

That which is claimed is:

1. In a process for separating at least one cycloalkane containing 5-10 carbon atoms per molecule from at least one close-boiling alkane by extractive distillation of a feed consisting essentially of said at least one cycloalkane and said at least one alkane, the improvement which comprises employing a solvent consisting essentially of a mixture of (a) at least one N-alkyl-2-pyrrolidone, wherein the alkyl group contains 1-3 carbon atoms per molecule, and (b) at least one glycol compound having the general chemical formula of HO—[CHR$^1$—CHR$^2$—O]$_n$—CHR$^1$—CHR$^2$—OH, wherein n can be 0, 1, 2, 3, or 4, and R$^1$ and R$^2$ are independently selected from the group consisting of hydrogen and the methyl group;

wherein said extractive distillation process produces (i) an overhead product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

2. A process in accordance with claim 1, wherein component (a) of said solvent is 2-methyl-2-pyrrolidone and component (b) of said solvent is selected from the group consisting of ethylene glycol, diethylene glycol, triethylene glycol, tetraethylene glycol and pentaethylene glycol.

3. A process in accordance with claim 2, wherein component (b) of said solvent is ethylene glycol.

4. A process in accordance with claim 2, wherein component (b) of said solvent is tetraethylene glycol.

5. A process in accordance with claim 1, wherein said at least one cycloalkane in said feed is cyclohexane.

6. A process in accordance with claim 1, wherein said at least one cycloalkane in said feed is cyclopentane.

7. A process in accordance with claim 1, wherein the weight ratio of component (b) to component (a) in said solvent is in the range of from about 0.2:1 to about 30:1.

8. A process in accordance with claim 7, wherein said weight ratio of component (b) to component (a) is in the range of from about 1:1 to about 10:1.

9. A process in accordance with claim 1, wherein said at least one cycloalkane in said feed is cyclohexane, component (a) in said solvent is N-methyl-2-pyrrolidone, component (b) in said solvent is selected from the group consisting of ethylene gylcol, diethylene glycol, triethylene glycol, tetraethylene glycol and pentaethylene glycol, and the weight ratio of component (b) to component (a) in said solvent is in the range of from about 0.2:1 to about 30:1.

10. A process in accordance with claim 9, wherein said component (b) in said solvent is ethylene glycol.

11. A process in accordance with claim 9, wherein component (b) in said solvent is tetraethylene glycol.

12. A process in accordance with claim 9, wherein component (b) in said solvent is tetraethylene glycol, and said weight ratio of component (b) to component (a) is in the range of from about 1:1 to 10:1.

13. A process in accordance with claim 1, wherein the weight ratio of said solvent to said feed is in the range of from about 0.5:1 to about 50:1.

14. A process in accordance with claim 1, wherein said feed boils at a temperature in the range of from about 80° F. to about 350° F., at a pressure of about 1 atm.

15. In a process for separating at least one cycloalkane containing 5-10 carbon atoms per molecule from at least one close-boiling alkane by extractive distillation of a feed consisting essentially of said at least one cycloalkane and said at least one alkane, the improvement which comprises employing a solvent consisting essentially of a mixture of
(a) at least one N-alkyl-2-pyrrolidone, wherein the alkyl group contains 1-3 carbon atoms per molecule,
(b) at least one glycol compound having the general chemical formula of $$HO\text{---}[CHR^1\text{---}CHR^2\text{---}O]_n\text{---}CHR^1\text{---}CHR^2\text{---}OH,$$

wherein n can be 0, 1, 2, 3, or 4, and $R^1$ and $R^2$ are independently selected from the group consisting of hydrogen and the methyl group, and
(c) about 1-3 weight-% water;
wherein said extractive distillation process produces (i) an overhead product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane that said feed; and wherein said at least one cycloalkane is separated from said solvent and recovered from said bottoms product.
(c) about 1-3 weight-% water.

16. A process in accordance with claim 15, wherein component (a) of said solvent is N-methyl-2-pyrrolidone, component (b) of said solvent is selected from the group consisting of ethylene glycol, diethylene glycol, triethylene glycol, tetraethylene glycol and pentaethylene glycol, and the weight ratio of component (b) to component (a) is in the range of from about 0.2:1 to about 30:1.

17. A process in accordance with claim 16, wherein said at least one cycloalkane is cyclohexane, and component (b) of said solvent is selected from the group consisting of ethylene glycol and tetraethylene glycol.

18. A process in accordance with claim 16, wherein said at least one cycloalkane is cyclopentane, and component (b) of said solvent is selected from the group consisting of ethylene glycol and tetraethylene glycol.

19. A process in accordance with claim 15, wherein the weight ratio of said solvent to said feed is in the range of from about 0.5:1 to about 50:1.

20. A process in accordance with claim 15, wherein said feed boils at a temperature in the range of from about 80° F. to about 350° F., at a pressure of about 1 atm.

* * * * *

UNITED STATES PATENT AND TRADEMARK OFFICE
CERTIFICATE OF CORRECTION

PATENT NO. : 4,948,472

DATED : August 14, 1990

INVENTOR(S) : Fu Ming Lee; Ronald E. Brown

It is certified that error appears in the above-identified patent and that said Letters Patent is hereby corrected as shown below:

Claim 15, Column 10, delete the entire line 3.
    Column 9, line 27, "that" should read --than--.

Signed and Sealed this

Twenty-eighth Day of January, 1992

Attest:

HARRY F. MANBECK, JR.

*Attesting Officer*      *Commissioner of Patents and Trademarks*